(12) United States Patent
Linker et al.

(10) Patent No.: US 6,604,406 B1
(45) Date of Patent: Aug. 12, 2003

(54) HUMAN PORTABLE PRECONCENTRATOR SYSTEM

(75) Inventors: Kevin L. Linker, Albuquerque, NM (US); Charles A. Brusseau, Tijeras, NM (US); David W. Hannum, Albuquerque, NM (US); James G. Puissant, Albuquerque, NM (US); Nathan R. Varley, Albuquerque, NM (US)

(73) Assignee: Sandia Corporation, Albuquerque, NM (US)

(*) Notice: Subject to any disclaimer, the term of this patent is extended or adjusted under 35 U.S.C. 154(b) by 51 days.

(21) Appl. No.: 09/917,017

(22) Filed: Jul. 26, 2001

Related U.S. Application Data

(63) Continuation-in-part of application No. 09/339,349, filed on Jun. 23, 1999.

(51) Int. Cl.[7] .............................. G01N 1/00; G01N 1/22; B01D 17/12; B01D 59/44; G08B 17/10
(52) U.S. Cl. ..................... 73/28.02; 73/28.01; 73/25.04; 73/863.23; 73/863.81; 422/88
(58) Field of Search ..................... 73/28.02, 28.04, 73/19.12, 28.01, 23.33, 23.2, 863.23, 863.71, 863.81; 422/78, 88

(56) References Cited

U.S. PATENT DOCUMENTS

| | | | | |
|---|---|---|---|---|
| 3,677,065 A | * | 7/1972 | Davis | 73/28 |
| 3,686,835 A | * | 8/1972 | Strange et al. | 73/270 |
| 4,149,402 A | * | 4/1979 | Manes | 73/23.1 |
| 4,247,311 A | * | 1/1981 | Seibert et al. | 55/162 |
| 4,544,386 A | * | 10/1985 | Trayford, III et al. | 55/270 |
| 4,670,137 A | * | 6/1987 | Koseki et al. | 210/96.1 |
| 4,790,650 A | * | 12/1988 | Keady | 356/37 |
| 4,803,869 A | * | 2/1989 | Barcelona et al. | 73/53 |
| 4,963,167 A | * | 10/1990 | Young et al. | 55/97 |
| 5,001,463 A | * | 3/1991 | Hamburger et al. | 340/627 |
| 5,054,328 A | * | 10/1991 | Long et al. | 73/864.81 |
| 5,092,218 A | * | 3/1992 | Fine et al. | 86/50 |
| 5,110,747 A | * | 5/1992 | Pataschnick et al. | 436/133 |
| 5,279,146 A | * | 1/1994 | Assano et al. | 73/28.04 |
| 5,449,294 A | * | 9/1995 | Bench et al. | 437/225 |
| 5,465,607 A | * | 11/1995 | Corrigan et al. | 73/23.36 |
| 5,763,360 A | * | 6/1998 | Gundel et al. | 502/402 |
| 5,834,628 A | * | 11/1998 | Hunter et al. | 73/28.04 |
| 5,854,431 A | * | 12/1998 | Linker et al. | 73/863.23 |
| 5,945,611 A | * | 8/1999 | Welker | 73/864.33 |
| 6,027,638 A | * | 2/2000 | Johnson | 210/86 |
| 6,057,165 A | * | 5/2000 | Mansour | 436/518 |

OTHER PUBLICATIONS

Linker, et al., "Human Portable Preconcentrator System," patent application No. 09/339,349, filed Jun. 23, 1999.

* cited by examiner

*Primary Examiner*—Helen Kwok
*Assistant Examiner*—David J. Wiggins
(74) *Attorney, Agent, or Firm*—Kevin W. Bieq; Russell D. Elliott

(57) ABSTRACT

A preconcentrator system and apparatus suited to human portable use wherein sample potentially containing a target chemical substance is drawn into a chamber and through a pervious screen. The screen is adapted to capture target chemicals and then, upon heating, to release those chemicals into the chamber. Chemicals captured and then released in this fashion are then carried to a portable chemical detection device such as a portable ion mobility spectrometer. In the preferred embodiment, the means for drawing sample into the chamber comprises a reversible fan which, when operated in reverse direction, creates a backpressure that facilitates evolution of captured target chemicals into the chamber when the screen is heated. The screen can be positioned directly in front of the detector prior to heating to improve detection capability.

14 Claims, 4 Drawing Sheets

HUMAN PORTABLE PRECONCENTRATOR SYSTEM

This application is a continuation-in-part of patent application Ser. No. 09/339,349 filed on Jun. 23, 1999, which is pending on appeal at the time that this application is filed.

This invention was made with Government support under Contract DE-AC04-94AL85000 awarded by the U.S. Department of Energy. The Government has certain rights in the invention.

BACKGROUND OF THE INVENTION

1. Field of the Invention

This invention relates to the field of particle concentrators, and more particularly to an apparatus and system for preconcentrating airborne particles to promote their detection. Specifically, the invention relates to a human portable particle preconcentrator system and apparatus that exhibits simple and reliable operation and is especially useful in conjunction with detecting compounds such as explosives, illegal drugs, other controlled substances and chemical agents. For purposes of this application, in the context of describing the claimed invention, the term particle is intended not to exclude vapor.

2. Description of the Related Art

Additional background information, supplemental to the information provided here, is found in U.S. Pat. No. 5,854,431 "Particle Preconcentrator" which is incorporated by reference herein in its entirety.

The detection of explosives, narcotics or other chemicals is a growing part of contraband detection. Recent years have seen rapid development of detectors capable of identifying the presence of explosives by capturing and identifying either vapors emanating from explosive materials or particles of explosive material, or both. Similarly, such detectors can also identify vapors and particles associated with other forms of contraband such as illegal drugs and other controlled substances. Such vapors and particles associated with contraband may be present and detectable on or near persons or objects that have been exposed to contraband materials and substances. Suitable detectors for this purpose include, but are not limited to, ion mobility spectrometers (IMS), electron capture detectors, and chemi-luminescence-based systems.

Detection of explosives, narcotics or other contraband substances demands reliable and convenient means for collecting and analyzing sample. For detection modalities such as those mentioned above, however, a challenge exists relating to accurately detecting and identifying target substances when only a small amount or small concentration of target chemical is present on or in proximity to a test subject. Often, collecting sample involves processing large volumes of diluent (for example, air) in order to obtain sufficient target chemicals for detection. The preconcentrator disclosed in the '431 patent offers one means for collecting trace amounts of target chemical in dilute concentration. There, target chemical is adsorbed onto at least one screen adapted to capture and concentrate particulate material and/or vapors entrained in a main gas flow. Then, using a secondary carrier gas flow, the concentrated target chemical is moved to a detector. The '431 device was designed to achieve the desired preconcentration of target chemicals while managing large amounts of air flow, in part, by using a system of chambers and valves. The present invention is simplified over the earlier technology and includes a number of features that are suited to convenient portability. For certain applications, the present invention offers a viable alternative to the preconcentrator described in the '431 patent.

A logical advance in the field of contraband detection has been the development of commercial portable detection instruments having hand-held (or otherwise human-portable) operating capabilities. Commercial manufacturers of portable detectors (such as IMS) have begun tuning their instruments to identify contraband substances. As noted, though, in many situations, the amount of chemical(s) available for sampling is small or in low concentration. Current methods for increasing sample concentration include wiping a surface to collect particulate residue or vacuuming a surface to collect particles and/or vapor. In both sampling methods, the collected sample is usually deposited on a paper or other substrate, perhaps treated with Teflon™ or another similar non-stick coating. According to one such method, sample collection involves physically rubbing (swiping) a substrate such as a felt on a surface of an object (herein referred to as a test subject) and then placing the substrate into the detector for analysis. An alternate sampling method is to vacuum the surface of a test subject (or the air around a test subject), pass the vacuumed air, containing sample, through a collector substrate, and again, place the collector substrate into the detector for analysis. In either case, these methods of sampling are time consuming and tedious, and they incur a cost for replacing the substrate. Additionally, especially where the swiping technique is used, there is a significant risk of sampling error if the amount of target chemicals present on a test subject is low, and the target chemicals are simply missed by the swipe. This is because it is generally impractical to swipe the entire surface of a test subject with a substrate.

Accordingly, a need remains for preconcentrator devices that are suitable to portable applications, that offer simplified operation as compared with existing technologies, and that effectively overcome challenges associated with obtaining and concentrating sample.

SUMMARY OF THE INVENTION

The human-portable preconcentrator system of the present invention provides a solution to the problems of collecting particulate and/or vapor sample and delivering it to the detector quickly. The system and apparatus disclosed here significantly reduce the overall collection and detection time by reducing, as compared with other technologies, the number of necessary manipulations and separate steps required in obtaining and testing sample. Additionally, the collection substrate within the human portable preconcentrator system need not be discarded or cleaned using labor-intensive techniques, prior to next use. Thus, the cost to obtain sample is reduced.

An advantage of the present invention is that it provides an apparatus for collecting particles entrained in a gas stream, the apparatus including: a body comprising a plenum, a first port through which gas with entrained particles can pass from a region outside of the body into the plenum, a second port and a third port; a fan adapted to draw gases through the plenum and second port; at least one pervious screen in a first position disposed across the second port; means for repositioning the at least one pervious screen to a second position disposed across the third port; and a connector adapted to permit joining the third port to a separate chemical detector.

Another advantage of the present invention is that it provides, a system for collecting and analyzing particles entrained in a gas stream, the system including elements similar to the apparatus just described, and also a detector adapted to draw gases from the plenum through the third port and perform chemical analysis of those gases.

Another advantage of the invention is that it provides a method of collecting and releasing target chemicals entrained in a gas, the method comprising the steps of: creating a first gas flow, having a first direction, to draw the gas with entrained target chemicals into a chamber and through at least one pervious screen whereby at least a portion of the target chemicals adhere to the at least one pervious screen, ceasing the first gas flow, and heating the at least one pervious screen thereby causing at least some of the chemicals that adhere to the at least one pervious screen to vaporize and evolve into the chamber.

Other objects, advantages and novel features will become apparent to those skilled in the art upon examination of the following description or may be learned by practice of the invention. The objects and advantages of the invention may be realized and attained by means of the instrumentalities and combinations particularly pointed out in the appended claims.

DESCRIPTION OF THE FIGURES

The accompanying drawings, which are incorporated into and form part of the specification, illustrate embodiments of the invention and, together with the description, serve to explain the principles of the invention.

DETAILED DESCRIPTION OF THE INVENTION

Figure 1:
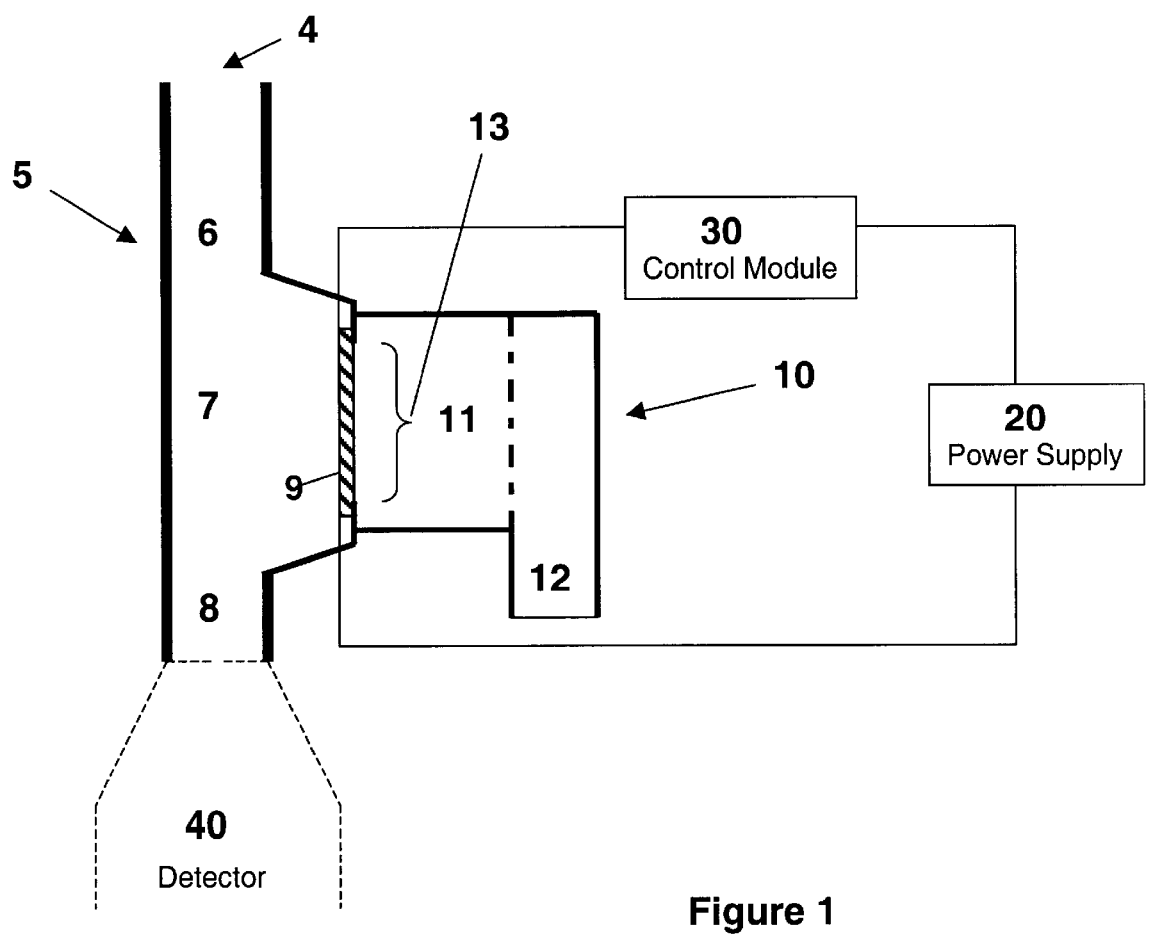
FIG. 1 is a schematic diagram showing elements of an apparatus according to one preferred embodiment of the claimed invention.

The present invention represents an improvement over prior vapor and particle preconcentrators for use in hand-held, or otherwise human-portable, applications. Advantageous features of the present invention include:

- the capability to function as a stand-alone system operating, optionally, on direct current (DC);
- uncomplicated air flows, including absence of valves or complex means for managing air flow;
- reusable sample collection means such as a reusable metal felt or screen to which target chemicals adhere during the first phase of operation of the invention; and
- a plenum having characteristics suited to providing increased concentration wherein the plenum is large enough to provide adequate airflow and low pressure drop, yet small enough to preconcentrate without the plenum having to be completely sealed or closed with valving.

For purposes of this disclosure, the invention "apparatus" generally refers to elements of the invention apart from a commercial portable detector instrument, such as a portable IMS. The invention "system" is generally intended to refer to the "apparatus" together with the commercial portable detector instrument.

In the preferred embodiment, the invention apparatus is used in conjunction with a portable detector such as the portable IMS detector mentioned above. The apparatus of the present invention is intended not to add significantly to the size, weight or bulkiness of such a detector, and may be adapted to conveniently attach to such a detector. A suitable portable power source includes either on-board batteries or, in the preferred embodiment, a separately portable battery pack similar to those used by operators of large video cameras and similar electronic equipment. Additionally, the preconcentrator apparatus and system of the present invention may include means for utilizing AC power such as from a conventional wall outlet, however, naturally in this instance, a user will be constrained to the extent that the electrical power cord limits freedom of movement.

It is noted that for purposes of the present disclosure, the term "air" is intended to include, as well, other gases or mixtures of gases that may contain target chemicals in dilute concentrations. It is recognized that the system and apparatus of the present invention could have applicability in environments wherein subjects to be tested could be located within environments containing ambient gases other than strictly "air." For convenience, however, the term "air" is used in this disclosure to refer to all such gases to the extent that they act as diluents from which target chemicals may be concentrated.

Sample is collected by manipulating an inlet port so that air is drawn into the apparatus from the space around a test subject or from the surface of the test subject. In this regard, the operation of the apparatus and system of the invention is similar to the vacuuming approach described in the background. In the case of the present invention, however, collection of sample is accomplished using an integrated screen or other adsorptive surface. The apparatus of the present invention also attaches directly to a detector, such as a commercial IMS detector. No added manipulation of collection substrate (such as removing the substrate and placing it inside a detector) is needed. The apparatus is designed to collect sample, concentrate the sample, and then deliver the sample to the detector for analysis in one substantially continuous operation.

The apparatus and system of the present invention function using a two-stage operation cycle. In the first stage or phase of operation, air containing target chemicals is collected in a fashion similar to that used with hand-held vacuuming devices well known, for example, in the cleaning industry. During this first phase, the air around the surface of a test subject is drawn into the preconcentrator apparatus, which includes a plenum, a fan (designated herein as a preconcentrator fan) and a collection screen. (The term "screen" used here is intended to include a variety of gas-pervious substrates. Suitable such substrates will be described in more detail, below.) Air passes through the plenum and then through the screen. If target substances are present in the sample, at least some of the entrained target chemicals adhere to the screen as the air passes through.

During the second stage of operation, the target chemicals (if any were present and collected from the sample), are driven off the screen, using heating alone or backpressure combined with heating of the screen. Preferably, the preconcentrator fan is reversed during the second stage of operation, causing a slight backpressure against the screen. At the same time, the screen is heated and a second fan inside of the commercial IMS unit or other detector is activated. The heating and backpressure cause target chemicals collected on the screen to evolve in vaporous phase back into the plenum. Target chemicals thus evolved will then be carried into the detector where they are subjected to chemical analysis. Alternatively, the screen can be repositioned to a second position in front of the detector port prior to heating. Alternatively, a swiped substrate may be placed in the screen position to enable the detection of samples that are collected by physically rubbing or swiping the surface of the test subject. The first stage of operation (referred to herein as the "adsorption cycle") preferably continues for a period of several seconds to as long as several minutes. The second stage (herein, the "desorption cycle) preferably takes from 0.1 to 1.5 seconds.

FIG. 1 illustrates diagrammatically the elements of a preferred embodiment of the invention. The preconcentrator comprises two main parts, a body 5 and a preconcentrator fan 10. The preconcentrator fan 10 in this embodiment needs to have a reversible air flow and preferably is a low volume/high pressure blower such a an AMETEK™ Model 116521-02. The invention has been successfully demonstrated using such a blower with a flow of 5 CFM at 12 in. $H_2O$. The preconcentrator fan 10 includes a first port 11 and a second port 12 which operate as inlet and outlet, or vice versa, depending on the direction of air flow in a given blower configuration. (It is noted that, commonly, reversal of air flow in fans is accomplished by reversing the direction of the fan motor, however, other methods of flow reversal may be possible and their existence is acknowledged. Any such methods are intended to fall within the scope of the appended claims where air flow reversal is recited.)

The body 5 may be made preferably of metal, plastic or any other light, durable material suitable for portable use. The material itself, also, must not release contaminant gases (out gas) at operating temperatures. The body 5 includes an inlet port 6, a plenum 7, and an outlet port 8. Preferably, the plenum 7 is generally cylindrical in shape and has a volume in the range of 2–3 $in^3$. Successful results have been demonstrated, for example, using a plenum having a volume of about 2.2 $in^3$. The plenum further includes a preconcentrator fan port 13 leading to the first port 11 of the preconcentrator fan 10. A pervious screen 9 is positioned over the preconcentrator fan port 13, preferably, so that the fan port 13 is covered and gases moving from the plenum 7 into the preconcentrator fan 10 must pass though the pervious screen 9.

The figure also shows a power supply 20 and control module 30 electrically connected to the screen 9. In the preferred embodiment, the power supply 20 is a DC power supply adapted to suit the portability of the apparatus. The control module 30 function includes a heating control, which, at a minimum, includes an on/off style switch for directing electrical current to the screen 9. In the preferred embodiment, when electrical current is delivered to the screen 9, it will heat up due to electrical resistance. Also, preferably, when the flow of electrical current to the screen 9 is discontinued, the screen 9 cools passively. Additionally, the apparatus must include a power supply for the preconcentrator fan 10 (preferably the same as power supply 20, although electrical connections to the preconcentrator fan are not shown in the Figure) and a switchable controller (not shown) that serves to activate the preconcentrator fan 10. The preconcentrator fan controller in the preferred embodiment can be used to cause the preconcentrator fan 10 to move air in a direction either from the first port 11 to the second port 12 (herein, the "forward direction"), or from the second port 12 to the first port 11 (herein, the "reverse direction"). Finally, the Figure illustrates the attachment of the body 5 of the preconcentrator to the inlet port of a portable detector 40, a portion of which is shown in phantom.

Figure 2:
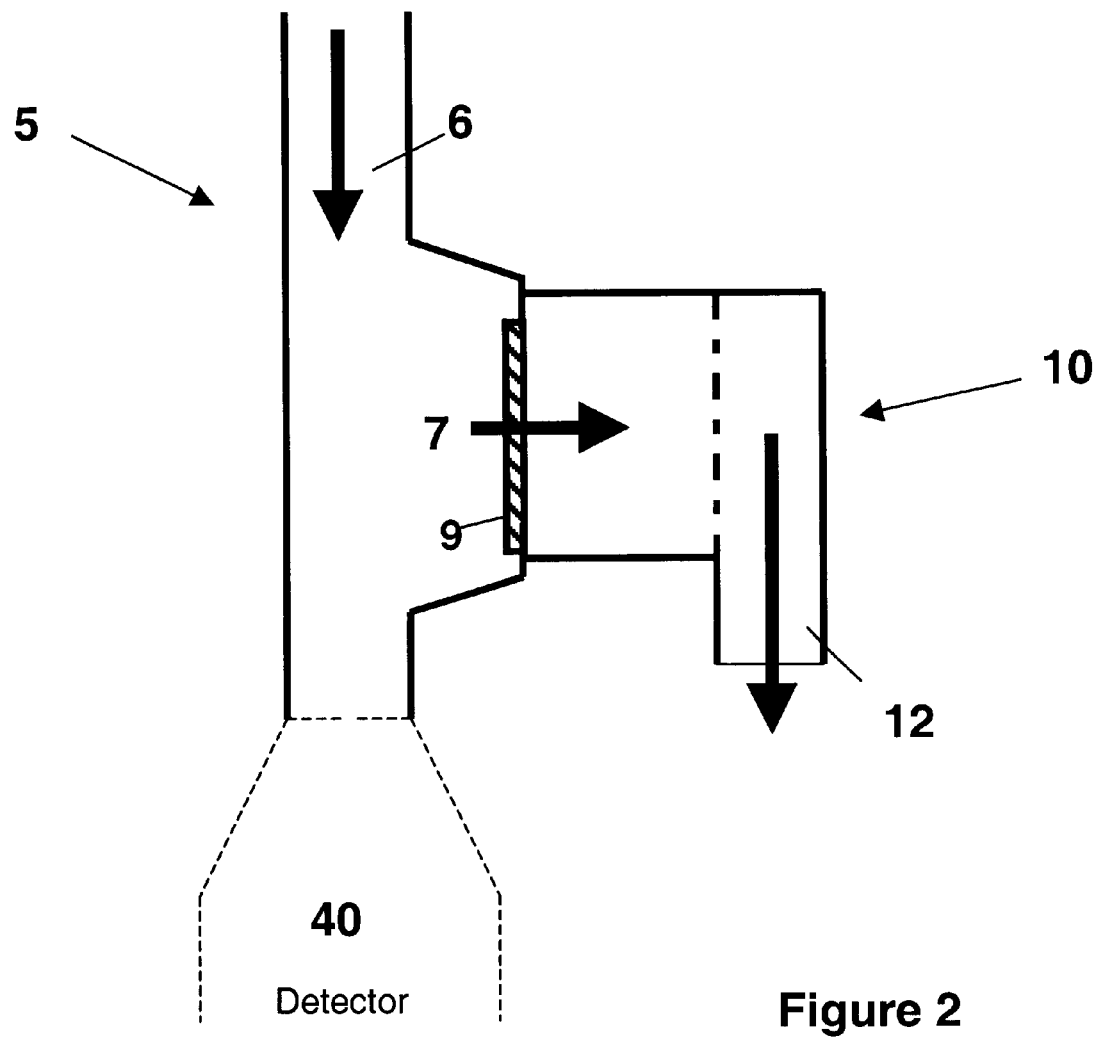
FIG. 2 is a schematic diagram showing direction of airflow during the first stage of operation of the apparatus of FIG. 1.

Referring now to FIG. 2, arrows are shown to illustrate the flow of gases through the system and apparatus of the present invention during the adsorption cycle. Specifically, during the adsorption cycle, the preconcentrator fan 10 is operated in the adsorption mode with gases flowing through the fan in a forward direction. As shown by the bold arrows in FIG. 2, when the preconcentrator fan 10 is so operated, air to be sampled for the presence of target chemicals is drawn into the preconcentrator body 5 via the inlet port 6. It passes through the plenum 7 and on though the screen 9. As the air passes through the screen 9 vapors and particulate matter entrained in the air adhere to the surface of the screen 9 and become concentrated thereon. The air then passes on through the preconcentrator fan 10 and ultimately exhausts through the second port 12.

It is noted that the figure shows a barrier (bold dotted line) between the plenum 7 of the preconcentrator and the detector 40. Whether such a barrier will be needed or desired in practice will depend in part on the characteristics of the detector being used. For example, it may be desirable to prevent air flow into the detector during the adsorption cycle of the preconcentrator operation, either because the detector may be damaged by suction created by the preconcentrator fan 10 or simply to ensure that any sample collected on the screen 9 was entrained in air flowing in through the inlet port 6 (rather than collected from another location, such as inside the detector 40). If the barrier is desired, it can include any suitable valve means capable of blocking airflow between the plenum 7 and the detector 40. As noted, though, in some circumstances such a barrier may not be needed.

Figure 3:
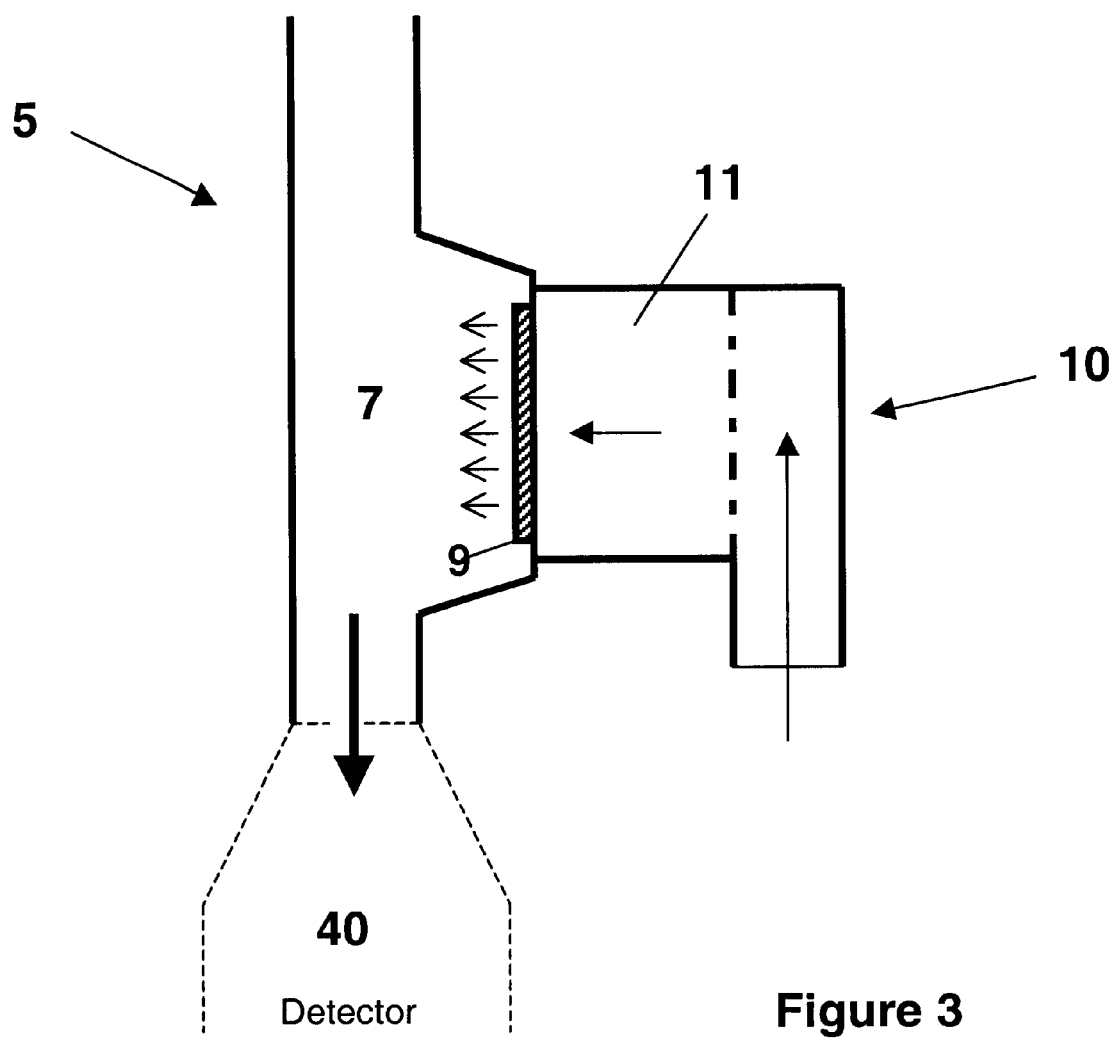
FIG. 3 is a schematic diagram showing direction of airflow during the second stage of operation of the apparatus of FIG. 1.

FIG. 3 illustrates aspects of the operation of the invention during the desorption phase of the operation cycle. During this phase, the preconcentrator fan 10 is operated in reverse direction so that a backpressure is created against the screen 9. This backpressure need only be slight, so the rate and volume of airflow of the preconcentrator fan when operated in the reverse direction need not be as great as when the preconcentrator fan is operated in the forward direction during the adsorption phase. There needs to be a space in which this backpressure can accumulate. As illustrated in the Figure, the first port 11 of the preconcentrator fan 10 can serve this function. The Figure depicts the direction of air flow in reverse direction, again, using arrows, however, the arrows are not as bold as those in FIG. 2, signifying that the rate and volume of air moved by the fan during the second phase of operation need not be as great as in the first phase.

At the same time as the preconcentrator fan 10 is operated in reverse direction, the screen 9 is heated. Heating of the screen causes adsorbed materials to vaporize and evolve off of the surface of the screen 9. This evolution of adsorbed materials is depicted using the series of light arrows pointing in a leftward direction in the Figure. The slight backpressure created by operation of the fan in reverse mode helps to drive the vaporized material into the plenum 7. At this stage, a fan in the commercial detector is activated which pulls gases (including vaporized substances formerly adhering to the screen) from the plenum into the detector 40 where they are subjected to analysis.

Figure 4:
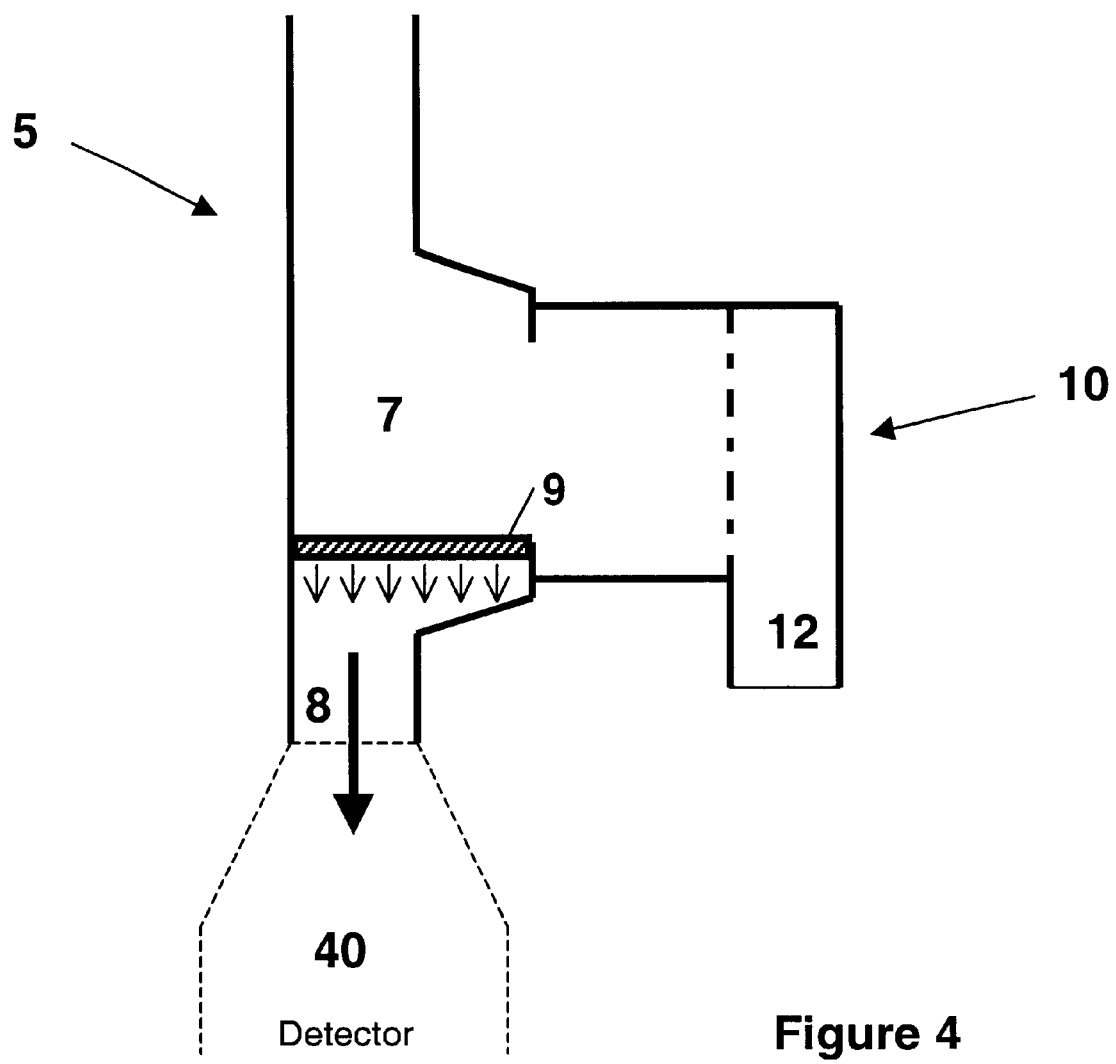
FIG. 4 is a schematic diagram showing the sample screen rotated to a position disposed across the third port during the second stage of operation of the apparatus of FIG. 1.

FIG. 4 illustrates an alternative embodiment of the invention wherein the screen 9 is repositioned to a second position in the outlet port 8, in front of the detector 40, prior to the heating of the screen. The repositioning can be done be removing the screen from the preconcentrator and reinserting it in the second position, or by rotating the screen from the first to the second position with a slip ring or other type of hinge without removing it from the preconcentrator. When the screen is heated in this second position and the fan in the commercial detector is activated, the desorption volume is effectively reduced from that depicted in FIG. 3, thereby increasing the sample concentration flowing into the detector during the desorption cycle and improving detection.

Finally, for sample collection that involves swiping a test object with a substrate, the swiped substrate may replace the screen and be placed in one of the positions described above for analysis by the detector 40.

It is noted that variations on the processes just described may be employed without departing from the general principles of the invention. For example, the apparatus may be operated with favorable results even if the preconcentrator fan 10 is not operated in reverse mode to create backpressure. Satisfactory desorption and evolution of vapors into the plenum 7 may be achieved simply by heating the screen 9. Also, it may not be necessary to turn the detector fan off and then on during the two separate phases (adsorption and desorption) or the operation cycle. It is expected that detectors are or may become available that are sufficiently durable, and exhibit sufficiently low intake air flow, to allow leaving the detector intake fan operating without either causing damage to the detector or interfering significantly with the adsorption phase of the preconcentrator operation cycle. Certainly, in principle, if some small percent of target chemicals collected were to pass directly from a test subject into the detector without preconcentration using the screen, there is a chance that they would be detected. If too much sample passes into the detector directly, however, the purpose of the preconcentrator will be defeated.

As was the case regarding the screen in the '431 patent mentioned above, the screen 9 of the present invention may include metal felt, woven wire mesh, or other pervious material to which particles and vapors may adsorb. Indeed, the screen in the present invention preferably exhibits all of the characteristics of the preferred screen of the '431 patent incorporated herein by reference. As described there, the screen 9 is substantially pervious to moving gases such as air. Preferably, the screen 9 is fashioned from an electrically conductive material, but which material is sufficiently resistive as to generate heat when electrical current is supplied. In the preferred embodiment, the screen 9 comprises a sheet of metal fiber felt material, such as one of the metal fiber matrices manufactured and sold by Bekaert Corporation, Research Triangle Park, North Carolina, USA, a subsidiary of Bekaert Fibre Technologies, Zwevegem, Belgium, under the trademarks Bekipor® ST 60AL3, Bekipor® ST 60AL3S, and Bekipor® ST 60AL3SS. In the preferred embodiment, a metallic felt screen 9 is used, preferably configured with zig-zag pleats to increase the collection surface area presented to the moving gas flows and reduce the pressure drop through the screen during the adsorb flow. Because metallic felts are highly efficient collectors, a single metallic felt screen 9 preferably is used in the invention. For example, but not by way of limitation, in one embodiment, the screen 9 comprises a sheet of Bekipor® ST AL3 metallic felt of about 5 ½ in$^2$, folded in an "accordion" fashion to form a pleated sheet about 1 ¼ in×1 ¼ in with a pleat peak-to-peak height of about ¼ inch and a pleat peak-to-peak separation of about 3/16 inches.

Alternatively, the screen 9 may comprise one or more sections of woven wire mesh, or in alternative embodiments of the invention not incorporating a heatable screen, the screens 9 may be fashioned from non-conductive materials pervious to gas, such as paper or cloth.

In designing a preconcentrator apparatus or system consistent with the principles disclosed herein certain factors must be considered in order to optimize performance. Below is provided an example of a design of a preconcentrator apparatus according to a preferred embodiment. Design considerations should, however, take into consideration the following factors:

1) A trade-off exists between high adsorption and pressure drops in the sample airflow stream. The surface area and porosity of the screen material (for example, metal felt) required to adsorb certain vapor and particles will determine the size (horsepower) of the preconcentrator fan needed. Different porosity metal felts are available, as are different woven wire meshes.

2) The overall size of the screen must be suited to the volume of the preconcentrator, and especially the preconcentrator plenum. Variation of the overall size of the screen (as well as its porosity) as compared with the volume of dead space in the plenum, for example, will affect the concentration ratio.

3) The duration of applying current (if at all) to the screen for heating directly impacts the available vapor to be transported to the detection device. For example, too much heating can result in destruction of sample.

An example of a functional preconcentrator constructed according to the claimed invention includes a unit having an internal volume of 2.2 in$^3$ with an inlet opening 4 having a diameter of one inch. Increasing the inlet size has a direct effect on the internal volume. Testing has determined that for the flow of 5 CFM though a one-inch opening provides adequate capture velocity and high levels of preconcentration of sample.

The particular sizes and equipment discussed above are cited merely to illustrate particular embodiments of the invention. It is contemplated that the use of the invention may involve components having different sizes and characteristics. It is intended that the scope of the invention be defined by the claims appended hereto. Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

We claim:

1. A portable flow-through preconcentrator apparatus for collecting particles entrained in a gas stream, the apparatus comprising:
   a main body including a plenum, a first port through which gas with entrained particles can pass from a region outside of the body in to the plenum, a second port and a third port,
   a fan adapted to draw gases through the plenum and second port,
   at least one pervious screen to collect the particles when the pervious screen is disposed in a first position across the second port and the gases are drawn through the second port by the fan,
   means for repositioning the at least one pervious screen from the first position to a second position disposed across the third port, and
   a connector adapted to permit joining the third port to a separate chemical detector.

2. The apparatus of claim 1 wherein the at least one pervious screen is adapted to be heatable in the second position.

3. The apparatus of claim 2 wherein the at least one pervious screen heats when electrical current is applied to it.

4. The apparatus of claim 3 further comprising at least one power source electrically connected to the at least one pervious screen.

5. The apparatus of claim 4 wherein the fan is further adapted to provide reversible air flows.

6. A portable flow-through preconcentrator system for collecting and analyzing particles entrained in a gas stream, the system comprising:
- a main body including a plenum, a first port through which gas with entrained particles can pass from a region outside of the body in to the plenum, a second port and a third port,
- a fan adapted to draw gases through the plenum and second port,
- at least one pervious screen to collect the particles when the pervious screen is disposed in a first position across the second port and the gases are drawn through the second port by the fan,
- means for repositioning the at least one pervious screen from the first position to a second position disposed across the third port, and
- a chemical detector adapted to draw gases from the plenum through the third port when the pervious screen is disposed in the second position across the third port and to perform chemical analysis of those gases.

7. The system of claim 6 wherein the at least one pervious screen is adapted to be heatable in the second position.

8. The system of claim 7 wherein the at least one pervious screen heats when electrical current is applied to it.

9. The system of claim 8 further comprising at least one power source functionally connected to the at least one pervious screen.

10. The system of claim 9 wherein the fan is further adapted to provide reversible air flows.

11. A portable flow-through preconcentrator apparatus for collecting particles entrained in a gas stream, the apparatus comprising:
- a main body including a plenum, a first port through which gas with entrained particles can pass from a region outside of the body in to the plenum, a second port and a third port,
- a fan adapted to draw gases through the plenum and second port,
- at least one pervious screen to collect the particles when the pervious screen is disposed in a first position across the second port and the gases are drawn through the second port by the fan,
- means for repositioning the at least one pervious screen from the first position to a second position disposed across the third port, wherein the repositioning means comprises a slip ring or rotatable hinge, and
- a connector adapted to permit joining the third port to a separate chemical detector.

12. The apparatus of claim 1, wherein the at least one pervious screen comprises a swiped substrate.

13. A portable flow-through preconcentrator system for collecting and analyzing particles entrained in a gas stream, the system comprising:
- a main body including a plenum, a first port through which gas with entrained particles can pass from a region outside of the body in to the plenum, a second port and a third port,
- a fan adapted to draw gases through the plenum and second port,
- at least one pervious screen to collect the particles when the pervious screen is disposed in a first position across the second port and the gases are drawn through the second port by the fan,
- means for repositioning the at least one pervious screen from the first position to a second position disposed across the third port, wherein the repositioning means comprises a slip ring or rotatable hinge, and
- a chemical detector adapted to draw gases from the plenum through the third port when the pervious screen is disposed in the second position across the third port and to perform chemical analysis of those gases.

14. The system of claim 6, wherein the at least one pervious screen comprises a swiped substrate.

* * * * *